United States Patent [19]

Fassi

[11] Patent Number: 5,952,379
[45] Date of Patent: Sep. 14, 1999

[54] STABLE, NON-HYGROSCOPIC SALTS OF L(-)CARNITINE AND ALKANOYL L(-) CARNITINES, A PROCESS FOR THEIR PREPARATION AND SOLID, ORALLY ADMINISTRABLE COMPOSITIONS CONTAINING SUCH SALTS

[75] Inventor: Aldo Fassi, Milan, Italy

[73] Assignee: Sigma-Tau Industrie Farmaceutiche, Riunite S.p.A, Italy

[21] Appl. No.: 09/194,608

[22] PCT Filed: May 26, 1997

[86] PCT No.: PCT/EP97/02693

§ 371 Date: Nov. 30, 1998

§ 102(e) Date: Nov. 30, 1998

[87] PCT Pub. No.: WO97/46512

PCT Pub. Date: Dec. 11, 1997

[30] Foreign Application Priority Data

May 31, 1996 [IT] Italy ................................. MI96A1116
Feb. 25, 1997 [IT] Italy ................................. MI97A0409

[51] Int. Cl.$^6$ ............................ A61K 31/20; C07C 69/34
[52] U.S. Cl. .......................... 514/561; 514/556; 560/196; 562/553
[58] Field of Search .................... 514/556, 561; 560/196; 562/553

[56] References Cited

U.S. PATENT DOCUMENTS 4,602,039  7/1986  Cavazza ................................. 514/561

FOREIGN PATENT DOCUMENTS

| 0 150 688 | 8/1985 | European Pat. Off. . |
| 0 434 088 | 6/1991 | European Pat. Off. . |
| 0 559 625 | 9/1993 | European Pat. Off. . |
| 0 637 449 | 2/1995 | European Pat. Off. . |
| 1 504 083 | 2/1968 | France . |

*Primary Examiner*—Shailendra Kumar
*Assistant Examiner*—Taylor Victor Oh
*Attorney, Agent, or Firm*—Nixon & Vanderhye

[57] ABSTRACT

Stable, non-hygroscopic salts of L(–)carnitine and alkanoyl L(–)carnitines with mucic acid of formula (I) are disclosed wherein the molar ratio between the carnitine moiety and mucic acid is 2:1. A process for producing the salts and solid orally administrable compositions containing same are also disclosed.

10 Claims, No Drawings

STABLE, NON-HYGROSCOPIC SALTS OF L(-)CARNITINE AND ALKANOYL L(-) CARNITINES, A PROCESS FOR THEIR PREPARATION AND SOLID, ORALLY ADMINISTRABLE COMPOSITIONS CONTAINING SUCH SALTS

The present invention relates to stable, non-hygroscopic salts of L(-)-carnitine and alkanoyl L(-)-carnitines, a process for their preparation and solid, orally administrable compositions containing such salts.

These salts lend themselves to the preparation of solid pharmaceutical compositions suitable for oral administration, such as pills, tablets, chewable tablets, capsules, granulates, powders and the like, of which L(-)carnitine or the alkanoyl L(-)carnitines, optionally formulated with the usual pharmacologically acceptable excipients, constitute the active ingredient.

These stable, non-hygroscopic salts also facilitate the production of solid compositions which may contain other active ingredients, e.g. with a nutritional and/or dietetic effect. These compositions which are administered orally constitute by far the most preferable administration form for a vast range of users and are increasingly establishing themselves on the so-called health food, medical food or nutraceutical market. These terms, which have yet to be rigorously defined from the regulatory point of view, denote foods or food components such as food supplements, dietetic products, energy foods, and the like, i.e. formulations which are not addressed to mainly or exclusively therapeutic purposes but which are aimed rather at enhancing well-being and at producing a general improvement in fitness and performance on the part of the consumer or at preventing metabolic disorders caused by dietary deficiencies or by the inadequate biosynthesis of essential endogenous substances as a result of advancing age.

The growing interest in L(-)carnitine and its derivatives in this field, too, stems from the increasingly widespread recognition, corroborated by scientific evidence, that L(-)carnitine and the lower alkanoyl L(-)carnitines, in addition to their well-known therapeutic value in the treatment of various diseases, make a marked contribution towards supplying energy to the skeletal musculature and increasing the resistance to prolonged, intense stress in professional athletes or in any subject practising sport also at amateur level, enhancing the performance capability of such subjects.

In addition, L(-)carnitine or its lower alkanoyl derivatives constitute indispensable nutritional supplements for vegetarians, whose diets have a low carnitine content as well as a low content of the two amino acids, lysine and methionine, which are the precursors of the biosynthesis of L(-)carnitine in the kidneys and liver.

The same considerations apply not only to those subjects who have to live on a diet poor in protein for prolonged periods of time, but, in general, also to those subjects who, though not presenting any clearly definable pathological condition, feel debilitated, experiencing a particular state of stress or physical and/or mental fatigue.

All these applications indicate that the solid orally administrable compositions are the preferred presentation form, inasmuch as they make it particularly easy for users to take the substances and comply with optimal dosage regimens.

Of growing interest, moreover, is the use of L(-)carnitine and its derivatives in the veterinary field and as animal feed supplements in the breeding of livestock, some species of fish, and, most notably, valuable animals such as racehorses and thoroughbreds.

It has long since been known that L(-)carnitine and its alkanoyl derivatives are extremely hygroscopic and not very stable when they occur as inner salts (or "betaines") as represented by the formula

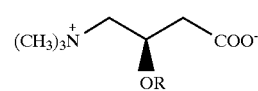

OR wherein R=H or $C_1$–$C_5$ lower alkanoyl.

This leads to complex problems of processing, stability and storage both of the raw materials and of the finished products. For example, L(-)carnitine tablets have to be packaged in blisters to keep them out of contact with the air, since, otherwise, even in the presence of normal humidity conditions, they would undergo alterations, swelling up and becoming pasty and sticky. In addition, owing to the inadequate stability, traces of trimethylamine are released which give the products an unpleasant fishy odour.

It is also known that the salts of L(-)carnitine and its alkanoyl derivatives present the same therapeutic, nutritional or dietetic activities, respectively, as the so-called inner salt (or "betaines") and can, therefore, be used in their place, provided these salts are "pharmacologically acceptable", i.e. they do not present unwanted toxic or side effects. In practice, then, the choice between an "inner salt" and a true L(-)carnitine or alkanoyl L(-)carnitine salt will depend essentially on pharmacy considerations rather than on therapeutic, nutritional or dietetic considerations.

The pharmaceutical technologist is indeed interested in having at his disposal salts of L(-)carnitine and its derivatives which, unlike the inner salts, are solid and stable, particularly even in conditions of prolonged storage, which are non-hygroscopic and therefore can be easily processed and formulated with the usual excipients, using blending, tabletting devices, etc., of a traditional type, and which, in addition, pose no packaging problems when converted into finished products. These salts, both in the form of raw materials and when formulated in finished products, should not, even in non-ideal storage conditions, release traces of trimethylamine which would have a repulsive effect on the user.

There is now an extensive body of literature, particularly patents, disclosing the production of stable, non-hygroscopic salts of L(-)carnitine and its derivatives.

Japanese patent No. 303067 (Tanabe Seiyaku), published on Jun. 19, 1962, publication No. 5199/19, discloses a process for the preparation of carnitine orotate, teaching that it is "advantageously less hygroscopic than carnitine and its typical salt, i.e. carnitine chloride, and can therefore be easily processed".

U.S. Pat. No. 4,602,039 (Sigma-Tau) granted on Jul. 22, 1986 discloses acid maleate and acid fumarate of L(-) carnitine.

French patent application No. 82 11626 (Sanofi) published on Jan. 6, 1984 publication No.2 529 545, discloses L(-)carnitine acid sulphate and acid oxalate as non-hygroscopic salts.

Finally, EP 0434088 (LONZA) discloses the use of the non-hygroscopic L(-)carnitine L(+)tartrate (2:1) (the preparation and physico-chemical characterization of which were however described by D. Müller and E. Strack in Hoppe Seyler's S. Physiol. Chem. 353, 618–622, April 1972) for the preparation of solid forms suitable for oral administration, such as tablets, capsules, powders or granulates.

All these L(-)carnitine salts, though being substantially less hygroscopic than the inner salt and affording more or less important advantages over the inner salt, nevertheless present certain drawbacks.

In the first place, fumaric, maleic and orotic acids form salts with L(−)carnitine wherein L(−)carnitine and the acid stand in an equimolar ratio, i.e. 1:1 and not 2:1. This constitutes a disadvantage, in that the percentage of the L(−)carnitine moiety, which is the one that exerts the beneficial therapeutic, nutritional or dietetic effects, is unsatisfactorily low compared to the portion that does not perform these functions and will be lower, the greater the molecular weight of the salifying acid used. Thus, for example, in L(−)carnitine orotate the L(−)carnitine amounts to only about 51%.

L(−)carnitine oxalate (also a 1:1 salt) is not used on account of the toxicity of oxalic acid.

L(−)carnitine tartrate, which presents the advantage of being a 2:1 salt (L(−)carnitine percentage: 68%) is not sufficiently stable for prolonged storage, releasing traces of trimethylamine which cause the above-mentioned highly disagreeable odour and becomes deliquescent at relative humidity slightly exceeding 60%.

In addition, none of the above-mentioned acids is capable of forming stable, non-hygroscopic salts with both L(−) carnitine and with the lower alkanoyl L(−)carnitines, particularly acetyl L(−)carnitine. Thus, for example, whereas L(−)carnitine acid fumarate and L(−)carnitine tartrate are easily crystallizable, non-hygroscopic compounds (see U.S. Pat. No. 4,602,039, Müller and Strack, loc. cit. and EP 0434088), acetyl L(−)carnitine acid fumarate and tartrate, respectively, are strongly hygroscopic compounds, which present the same drawbacks as the corresponding inner salts.

The present invention provides pharmacologically acceptable salts of L(−)carnitine and alkanoyl L(−)carnitines which present neither the drawbacks of hygroscopicity, poor stability during storage, processing difficulties and packaging problems of the corresponding inner salts nor the above-mentioned drawbacks of the known non-hygroscopic salts.

In particular, the present invention provides solid, non-hygroscopic salts which are stable and do not release traces of trimethylamine even in storage conditions far more extreme (in terms of duration, temperature and relative humidity percentage) than those borne by the known salts. In addition, the non-hygroscopic salts of the invention present the same anion both in the L(−)carnitine salt and in the alkanoyl L(−)carnitine salts. In all these salts, the molar ratio between the L(−)carnitine moiety and the acid moiety is 2:1.

The salts of the invention are salts of L(−)carnitine and alkanoyl L(−)carnitine with mucic acid having the formula (I):

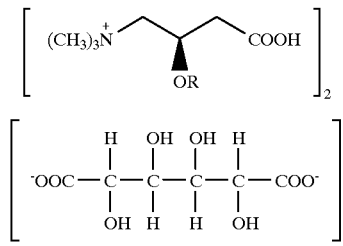

wherein R is hydrogen or a straight or branched alkanoyl group having 2–12 carbon atoms.

Preferably, the alkanoyl group is a lower alkanoyl group having 2–5 carbon atoms.

Even more preferably, the lower alkanoyl group is selected from acetyl, propionyl, butyryl, valeryl and isovaleryl.

L(−)carnitine mucate (2:1), acetyl L(−)carnitine mucate (2:1), propionyl L(−)carnitine mucate (2:1) and isovaleryl L(−)carnitin mucate (2:1) are examples of particularly preferred salts according to the present invention.

Mucic acid (or galactaric acid) as well as its salts are atoxic compounds.

Indeed, ammonium mucate has been proposed to replace potassium bitartrate in backing powder and for manufacturing granular effervescing salts. Moreover, mucate anion is encompassed in the list of the FDA-approved commercially marketed salts (see Journal of Pharmaceutical Sciences, vol. 66 no. 1, January 1977, page 3).

Also the process of the present invention presents distinct advantages over the prior art processes.

The known processes entail the use of large volumes of water or hydroalcoholic mixtures or organic solvents (such as methanol, ethanol, isobutanol) wherein L(−)carnitine inner salt and/or the suitable acid [e.g. L(+) tartaric or fumaric acid] are dissolved for carrying out the salification and the subsequent crystallization. For instance, according to the previously cited EP 0434088, a boiling solution of L(+)tartaric acid in aqueous 90% ethanol is prepared and L(−)carnitine inner salt is then added thereto. This makes it necessary to concentrate large volumes of the carnitine salt-containing solution at high temperatures (50–60° C.) under reduced pressure (about 200 Torr), with attendant noticeable energy waste. Moreover, the use of organic solvents entail high costs and serious problems of solvent recycling, environmental pollution and disposal of toxic waste materials.

The process of the present invention overcomes the drawbacks of the known processes, as it will be apparent from the following detailed description thereof.

The process of the present invention for preparing the solid, non-hygroscopic and stable salts of formula (I) comprises:

(a) mixing at room temperature L(−)carnitine inner salt or an alkanoyl L(−)carnitine inner salt wherein the alkanoyl is as previously defined with the least amount of water necessary to obtain a slurry of pasty or semiliquid consistency;

(b) adding to the slurry at room temperature mucic acid in a molar amount which is one-half the molar amount of L(−)carnitine or the aforesaid alkanoyl L(−)carnitine inner salt and thoroughly blending the resulting reaction mixture;

(c) carrying out the solidification/dehydration of the reaction mixture by letting the reaction mixture to stand in the open air at relative humidity not higher than 50% or accelerating the solidification/dehydration thereof by drying means; and (d) optionally grinding the solidified reaction mixture to provide the salt as a granulate or powder product.

In carrying out step (c), if it is preferred to accelerate the solidification/dehydration of the reaction mixture obtained in step (b), instead of letting the reaction mixture to stand, it can be fed into a continues drier or batch drier such as a turbotray drier, direct-heat rotary drier, drum drier, belt drier, spray drier, fluid bed drier and similar industrial driers well known to those skilled in chemical technology (see. e.g. "Drying" in Kirk-Othmer's Encyclopedia of Chemical Technology, vol. 8, pages 91–112, 1979).

Alternatively, the dehydration of the reaction mixture can be carried out by treating it with a very small volume of a non-toxic volatile, water-miscible solvent wherein L(−) carnitine and alkanoyl L(−)carnitine mucates are insoluble, such as e.g. acetone.

The following non-limiting examples show the preparation of the mucates of L(-)carnitine and some alkanoyl L(-)carnitines according to the process of the present invention as well as their physico-chemical characteristics.

EXAMPLE 1
L(-)carnitine Mucate (2:1)

(1.a) 161.2 g (1.0 mole) of L(-)carnitine inner salt and 30 mL of distilled water were mixed in a mortar to obtain a semiliquid slurry.

105.1 g (0.5 moles) of mucic acid were added to the slurry and the resulting mixture was thoroughly blended with a pestle. Upon homogenization, a semitransparent, sticky and whitish "cream" formed which could be evenly spread on the bottom and walls of the mortar. In order to accelerate the solidification of the mucate thus formed the product was exposed to the air stream of a fan (air relative humidity about 40–45%, room temperature about 22° C.). After 15–20 minutes, the solidified L(-)carnitine mucate could be ground to the wanted particle By repeating the aforesaid preparation several times, it was consistently found that the water content of the end product [L(-)carnitine mucate (2:1)] was 1.7–1.9% by weight.

Yield: 100% IR (KBr) $cm^{-1}$ 3500–3000 (OH), 1726 (COOH); 1594 (COO$^-$); 1244 (C—O $sp^2$); 1106–1048 (C—O $Sp^3$)

$^1$H-NMR (200 MHz, DMSO-$d_6$, ppm from TMS): 2.10–2.35 (m, 4H, $CH_2COO$); 3,14 (s, 18H, $(CH_3)_3$—$N^+$); 3,32 (d, 4H, $CH_2$—$N^+$); 3.62 (s, 2H, (C$\underline{H}$OH—CHOH—COOH)$_2$); 3.95 (s, 2H, (CHOH—C$\underline{H}$OH—COOH)$_2$); 4.31–4.37 (m, 2H, $CH_2$—C$\underline{H}$—$CH_2$); 4.86–5.21 (m, 8H, OH)

Analysis for $C_{20}H_{40}N_2O_{14}$ Calculated: C 45.10 H 7.57 N 5.25 Found: C 44.97 H 7.54 N 5.33

(1.b) It was also shown that L(-)carnitine mucate solidification and water removal till a groundable product was obtained, occurred also spontaneously after some hours by simply letting the product to stand, i.e. without exposing the product to any air stream.

(1.c) Alternatively, the slurry of L(-)carnitine and mucic acid was homogenized with a spatula on a glass plate instead of mixing the slurry with a pestle in a mortar.

The resulting mucate was spread on the glass plate to form a thin layer in order to promote the spontaneous water removal. The result was similar to that described in (1.b); however, water removal occurred in a shorter time.

L(-)carnitine content, calculated on the anhydrous product, is 60.5% in all the foregoing cases.

EXAMPLE 2
L(-)carnitine Mucate (2:1)

16.2 g (0.1 moles) of L(-)carnitine inner salt and 3 mL of distilled water were mixed in a mortar to obtain a semiliquid slurry. 10.5 g (0.05 moles) of mucic acid were added to the slurry and the resulting mixture was thoroughly homogenized with a pestle until a semitransparent, sticky and withish "cream" formed.

When the "cream" started to solidify, 70 mL of acetone were added thereto while mixing with the pestle was continued. Shortly thereafter the mucate was obtained as a finely powder-like solid which was filtered off, washed with further 30 mL of acetone and dried under vacuum at room temperature.

The compound thus obtained was pratically anhydrous.

Yield: higher than 99%.

EXAMPLE 3
Acetyl L(-)carnitine Mucate (2:1)

203.2 g (1.0 mole) of acetyl L(-)carnitine inner salt and 35 mL of distilled water were mixed in a mortar to obtain a semiliquid slurry. 105.1 g (0.5 moles) of mucic acid were then added to the slurry. The same procedure as that of Example 1 was then followed. The reaction mixture behaviour was the same as that of Example 1.

By repeating this preparation several times, it was consistently found that the water content of the end product [acetyl L(-)carnitine mucate (2:1 )] was 2.7–3.1% by weight.

Yield: 100%. The content of acetyl L(-)carnitine, calculated on the anhydrous product, is 65.9%.

IR (KBr) $cm^{-1}$ 3500–3000 (OH), 1740 ($COCH_3$, COOH); 1592 (COO$^-$), 1234 (C—O $sp^2$); 1106–1048 (C—O $sp^3$)

$^1$H-NMR (200 MHz, DMSO-$d_6$, ppm from TMS); 2,05 (s, 6H, $COCH_3$); 2.3–2.6 (m, 4H, $CH_2COO$); 3.11 (s, 18H, $(CH_3)_3$—$N^+$); 3.61 (s, 2H, (C$\underline{H}$OH—CHOH—COOH)$_2$); 3.67–3.73 (m, 4H, $CH_2$—$N^+$); 3.95 (s, 2H, (CHOH—C$\underline{H}$OH—COOH)$_2$); 5.36–5.42 (broad m, 8H, $CH_2$—C$\underline{H}$—$CH_2$ and OH)

Analysis for $C_{24}H_{44}N_2O_{16}$ Calculated: C 46.74 H 7.19 N 4.54 Found: C 46.62 H 7.14 N 4.61

EXAMPLE 4
Propionyl L(-)carnitine Mucate (2:1)

217.2 g (1.0 mole) of propionyl L(-)carnitine inner salt and 35 mL of distilled water were mixed in a mortar to obtain a semiliquid slurry. 105.1 g (0.5 moles) of mucic acid were then added to the slurry. The same procedure as that of Example 1 was then followed. The reaction mixture behaviour was the same as that of Example 1. By repeating this preparation several times, it was consistently found that the water content of the end product [propionyl L(-)carnitine mucate (2:1)] was 2.4–2.9% by weight.

Yield: 100%. The content of propionyl L(-)carnitine, calculated on the anhydrous product, is 67.4%.

IR (KBr) $cm^{-1}$ 3500–3000 (OH), 1738 ($COCH_2CH_3$, COOH), 1590 (COO$^-$), 1240 (C—O $sp^2$), 1104–1040 (C—O $sp^3$)

$^1$H-NMR (200 MHz, DMSO-$d_6$, ppm from TMS); 1,03 (t, 6H,$CH_2$C$\underline{H}_3$); 2.2–2.6 (m, 8H, C$\underline{H}_2$$CH_3$ and $CH_2COO$); 3.11 (s, 18H, $(CH_3)_3$—$N^+$); 3.62 (s, 2H, (C$\underline{H}$OH—CHOH—COOH)$_2$); 3.67–3.80 (m, 4H, $CH_2$—$N^+$); 3.96 (s, 2H, (CHOH—C$\underline{H}$OH—COOH)$_2$); 5.30–5.45 (broad m 8H, $CH_2$—C$\underline{H}$—$CH_2$ and OH)

Analysis for $C_{26}H_{48}N_2O_{16}$ Calculated: C 48.44 H 7.50 N 4.34 Found: C 48.22 H 7.44 N 4.25

EXAMPLE 5
Isovaleryl L(-)carnitine Mucate (2:1)

245.2 g (1.0 mole) of isovaleryl L(-)carnitine inner salt and 38 mL of distilled water were mixed in a mortar to obtain a semiliquid slurry. 105.1 g (0.5 moles) of mucic acid were then added to the slurry. The same procedure as that of Example 1 was then followed. The reaction mixture behaviour was the same as that of Example 1.

By repeating this preparation several times, it was consistenly found that the water content of the end product [isovaleryl L(-)carnitine mucate (2:1)] was 3.3–3.7% by weight.

Yield: 100%. The content of isovaleryl L(-)carnitine, calculated on the anhydrous product, is 70.0%.

It will be apparent that the moisture content of the end product depends on many factors such as the moisture content of the starting L(-)carnitine or alkanoyl L(-)carnitine, the temperature and relative humidity of the air in the plant where the production operations are carried out, the overall processing duration and the particle size of the final product.

It will also be apparent that the present process presents several, noticeable advantages over the prior art processes:

a) the process is carried out at room temperature and ambient pressure;

b) no organic solvents (or very small amounts thereof) are used, thus environmental pollution is avoided;

c) the yield is pratically quantitative;

d) starting from anhydrous L(−)carnitine or alkanoyl L(−)carnitine inner salt is not required: it is sufficent that their initial moisture content is known;

e) the consistency of the starting mixture can be varied, from a semisolid slurry to dense slurries of varying flowability, by simply regulating the added amount of water (10% to 30% by weight of the whole slurry). This allows a selection among the dehydration procedures to be made: from spontaneous water evaporation carried out in an environment at low relative humidity (e.g. 30–40%) to accelerated water removal by the aforesaid industrial driers.

The compositions of the present invention may occur as pharmaceutical compositions, over-the-counter (OTC) compositions, food supplements, dietary supplements, health foods, medical foods, nutraceuticals, veterinary products and fodders.

The compositions of the present invention may optionally comprise, in addition to the usual excipients, fillers, binding agents, lubricants, mould release agents, flow regulating agents, colorants and flavouring agents, as well as other active ingredients such as vitamins, aminoacids, trace elements, mineral substances and the like.

The compositions may occur in unit dosage form as tablets, chewable tablets, pills, pellets, troches, and capsules, which comprise an amount of a salt of formula (I) corresponding to 50–1000 mg, preferably 100–500 mg, of L(−) carnitine inner salt or alkanoyl L(−)carnitine inner salt, respectively.

For use in the veterinary field or as fodder, powders and granulates are preferred.

Some examples of compositions in unit dosage form are hereinbelow described.

(a) Composition for chewable tablets of L(-)carnitine mucate

One chewable tablet contains:
Active ingredient

| | |
|---|---|
| L(−)carnitine mucate (corresponding to 1 g of L(-)carnitine inner salt) | g 1.650 |
| Excipients: | |
| Peppermint flavour powder | g 0.075 |
| Licorice flavour powder | g 0.075 |
| Saccharose | g 1.730 |
| Corn starch | g 0.090 |
| Magnesium stearate | g 0.090 |

(b) Composition for tablets of acetyl L(-)carnitine

One tablet contains:
Active ingredient:

| | |
|---|---|
| Acetyl L(−)carnitine mucate (corresponding to 500 mg of acetyl L(-)carnitine inner salt) | mg 759 |

-continued

Excipients microcrystalline cellulose, polyvinylpyrrolidone, magnesium stearate, cellulose, acetate phthalate, diethylphthalate, dimethicone.

(c) Compositions for tablets of propionyl L(-)carnitine mucate

One tablet contains:
Active ingredient

| | |
|---|---|
| propionyl L(−)carnitine mucate (corresponding to 500 mg of propionyl L(-)carnitine inner salt) | mg 635 |
| Excipients | |
| microcrystalline cellulose | mg 54.0 |
| polyvinylpyrrolidone | mg 18.0 |
| crospovidone | mg 30.0 |
| magnesium stearate | mg 15.0 |
| precipitated silica | mg 3.0 |
| hydroxypropylmethylcellulose | mg 10.0 |
| polyethylene glycol 6000 | mg 2.5 |
| titanium dioxide | mg 1.8 |
| methacrylate copolymer | mg 8.3 |
| purified talc | mg 2.4 |

I claim:

1. A salt having the formula (I):

$$\left[ (CH_3)_3\overset{+}{N} \diagdown \diagup COOH \atop OR \right]_2$$

$$\left[ {}^-OOC-\underset{OH}{\overset{H}{\underset{|}{C}}}-\underset{H}{\overset{OH}{\underset{|}{C}}}-\underset{H}{\overset{OH}{\underset{|}{C}}}-\underset{OH}{\overset{H}{\underset{|}{C}}}-COO^- \right]$$

wherein R is hydrogen or a straight or branched alkanoyl group having 2–12 on atoms.

2. The salt of claim 1, wherein the alkanoyl group is a lower alkanoyl group having 2–5 carbon atoms.

3. The salt of claim 2, wherein the lower alkanoyl group is selected from acetyl, propionyl, butyryl, valeryl and isovaleryl.

4. A salt of claim 1, selected from the group comprising L(−)carnitine mucate (2:1), acetyl L(−)carnitine mucate (2:1), propionyl L(−)carnitine mucate (2:1) and isovaleryl L(−)carnitine mucate (2:1).

5. A process for producing a salt of formula (I):

$$\left[ (CH_3)_3\overset{+}{N} \diagdown \diagup COOH \atop OR \right]_2$$

$$\left[ {}^-OOC-\underset{OH}{\overset{H}{\underset{|}{C}}}-\underset{H}{\overset{OH}{\underset{|}{C}}}-\underset{H}{\overset{OH}{\underset{|}{C}}}-\underset{OH}{\overset{H}{\underset{|}{C}}}-COO^- \right]$$

wherein R is hydrogen or a straight or branched alkanoyl group having 2–12, carbon atoms, which comprises:

(a) mixing at room temperature L(−)carnitine inner salt or an alkanoyl L(−)carnitine inner salt wherein the alkanoyl is as previously defined with the least amount of water necessary to obtain a pasty or semiliquid slurry;

(b) adding to the slurry at room temperature mucic acid in a molar amount which is one-half the molar amount of L(−)carnitine or the aforesaid alkanoyl L(−)carnitine inner salts and thoroughly blending the resulting reaction mixture:

(c) carrying out the solidification/dehydration of the reaction mixture by letting the reaction mixture to stand in the open air at relative humidity not higher than 50% or accelerating the solidification/dehydration thereof by drying means; and (d) optionally grinding the solidified reaction mixture to provide the salt as a granulate or powder product.

6. The process of claim 5, wherein the drying means are selected from a continuous drier, a batch drier, a turbotray drier, a direct-heat rotary drier, drum drier, a belt drier, a spray drier and a fluid-bed drier.

7. A solid, orally administrable composition which comprises a salt having the formula (I)

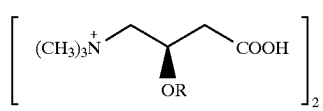
(I)

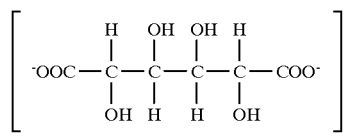

wherein R is hydrogen or a straight or branched alkanoyl group having 2–12, carbon atoms, and, optionally, a pharmacologically acceptable excipient.

8. The composition of claim 7 as a pharmaceutical composition, OTC composition health food, medical food, nutraceutical, diet supplement, nutritional supplement, veterinary product or fodder.

9. The composition of claim 8 in the form of a tablet, chewable tablet, pill, pellet, troche, capsule, powder or granulate.

10. The composition of claim 7 in unit dosage form, which comprises an amount of a salt of formula (I) corresponding to 50–1000 mg, of L(−)carnitine inner salt, or alkanoyl L(−)carnitine inner salt, respectively.

* * * * *